United States Patent [19]

Bernstein

[11] Patent Number: 5,747,482
[45] Date of Patent: May 5, 1998

[54] METHODS AND COMPOSITIONS TO INHIBIT KERATINOCYTE PROLIFERATION

[76] Inventor: Lawrence R. Bernstein, 380 Willow Rd., Menlo Park, Calif. 94025

[21] Appl. No.: 688,565

[22] Filed: Jul. 30, 1996

[51] Int. Cl.$^6$ ............................................. A61K 31/555
[52] U.S. Cl. ................... 514/184; 514/859; 514/861; 514/863; 514/864
[58] Field of Search ....................... 424/650; 514/184, 514/859, 861, 863, 864

[56] References Cited

U.S. PATENT DOCUMENTS

| | | | |
|---|---|---|---|
| 4,529,593 | 7/1985 | Warrell, Jr. et al. | 424/127 |
| 4,596,710 | 6/1986 | Collery | 424/131 |
| 4,704,277 | 11/1987 | Bockman et al. | 424/131 |
| 5,175,006 | 12/1992 | Matkovic et al. | 424/650 |
| 5,258,376 | 11/1993 | Bernstein | 514/184 |

FOREIGN PATENT DOCUMENTS

WO 91/10437  7/1991  WIPO.

OTHER PUBLICATIONS

Adamson, et al., "Studies on the Antitumor Activity of Gallium Nitrate (NSC–15200) and Other Group IIIa Metal Salts", *Chemotherapy Reports*, Part 1, 59:599–610 (1975).

Landegren, "Measurement of Cell Numbers by Means of the Endogenous Enzyme Hexosaminidase. Applications to Detection of Lymphokines and Cell Surface Antigens", *J. Immunol. Methods*, 67:379–388 (1984).

Matkovic, et al., "Gallium Prevents Adjuvant Arthritis in Rats and Interferes with Macrophage/T–Cell Function in the Immune Response", *Current Therap. Res.*, 50(2):255–267 (1991).

Whitacre, et al., "Suppression of Experimental Autoimmune Encephalomyelitis by Gallium Nitrate", *J. Neuroimmuno.*, 39:175–182 (1992).

Warrell, Jr. et al., "Gallium in the Treatment of Hypercalcemia and Bone Metastasis", in *Important Advances in Oncology 1989*, DeVita, Jr., Editor, J.P. Lippincott Company, Philadelphia, PA. (1989).

Wilkinson, et al., "Nerve Growth Factor Increases the Mitogenicity of Certain Growth Factors for Cultured Human Keratinocytes: A Comparison with Epidermal Growth Factor", *Exper. Dermatol.*, 3:239–245 (1994).

*Primary Examiner*—Kimberly Jordan
*Attorney, Agent, or Firm*—Burns, Doane, Swecker & Mathis, L.L.P.

[57] ABSTRACT

Disclosed are methods to inhibit mammalian skin cell proliferation and, in particular, human keratinocyte proliferation by the topical administration of neutral gallium complexes.

17 Claims, 7 Drawing Sheets

METHODS AND COMPOSITIONS TO INHIBIT KERATINOCYTE PROLIFERATION

BACKGROUND OF THE INVENTION

1. Field of the Invention

This invention is directed, in part, to methods to inhibit mammalian skin cell proliferation and, in particular, human keratinocyte proliferation. In the methods of this invention, the topical administration of neutral gallium complexes, when employed above certain concentrations, have been found to significantly inhibit keratinocyte proliferation.

This invention is also directed, in part, to methods for the treatment or prevention of disease conditions, such as psoriasis, which are characterized by excessive proliferation of keratinocytes.

This invention is still also directed, in part, to pharmaceutical compositions suitable for topical application which compositions comprise specified neutral gallium complexes.

2. References

The following publications, patents and patent applications are cited in this application as superscript numbers:

[1] Warrell, Jr. et al., U.S. Pat. No. 4,529,593 for "Use of Gallium Salts to Treat Disorders of Calcium Homeostasis, issued Jul. 16, 1985

[2] Warrell, Jr. et al., "Gallium in the Treatment of Hypercalcemia and Bone Metastasis", in "Important Advances in. Oncology 1989", DeVita, Jr., Editor, J. P. Lippincott Company, Philadelphia, Pa.

[3] Bockman, et al., U.S. Pat. No. 4,704,277 for "Methods for Treating Bone Disorders", issued Nov. 3, 1987

[4] Collery, U.S. Pat. No. 4,596,710 for "Gallium Chloride as a New Anti-Cancer Drug", issued Jun. 24, 1986

[5] Adamson, et al., "Studies on the Antitumor Activity of Gallium Nitrate (NSC-15200) and Other Group IIIa Metal Salts", Chemotherapy Reports, Part 1, 59:599–610 (1975)

[6] Bockman, et al., International Patent Application Publication No. WO 91/10437, for "Methods of Enhancing Wound Healing and Tissue Repair", published Jul. 25, 1991.

[7] Whitacre, et al., "Suppression of Experimental Autoimmune Encephalomyelitis by Gallium Nitrate", J. Neuroimmuno., 39:175–182 (1992)

[8] Matkovic, et al., U.S. Pat. No. 5,175,006 for "Method of Treating Arthritis Using Gallium Compounds", issued Dec. 29, 1992

[9] Matkovic, et al., "Gallium Prevents Adjuvant Arthritis in Rats and Interferes with Macrophage/T-Cell Function in the Immune Response", Current Therap. Res., 50(2) :255–267 (1991)

[10] Bernstein, U.S. Pat. No. 5,258,376 (1993) for "Pharmaceutical Compositions of Gallium Complexes of 3-Hydroxy-4-Pyrones", issued Nov. 2, 1993

[11] Wilkinson, et al., "Nerve Growth Factor Increases the Mitogenicity of Certain Growth Factors for Cultured Human Keratinocytes: A Comparison with Epidermal Growth Factor" Exper. Dermatol., 3:239–245 (1994)

[12] Landegren, "Measurement of Cell Numbers by Means of the Endogenous Enzyme Hexosaminidase. Applications to Detection of Lymphokines and Cell Surface Antigens", J. Immunol. Methods, 67:379–388 (1984)

All of the above publications, patents and patent applications are herein incorporated by reference in their entirety to the same extent as if each individual publication, patent or patent application was specifically and individually indicated to be incorporated by reference in its entirety.

State of the Art

Gallium salts are disclosed in the art as being useful in the treatment of many human and other mammalian diseases, including hypercalcemia, cancer, and certain degenerative or metabolic bone diseases such as osteoporosis and Paget's disease.[1-5] Gallium is also disclosed to mimic the molecular action of transforming growth factor-β, including stimulation of the growth of keratinocytes in the skin at low concentrations, thereby finding utility in promoting wound healing, and tissue repair.[6] Other reported uses for gallium include the suppression of experimental autoimmune encephalomyelitis[7]; the prevention of rheumatoid athritis[8]; and interference with macrophage/T-cell function in the immune response.[9]

In such treatments, gallium itself appears to be the active agent; the form in which the gallium is administered (e.g., as the nitrate, sulfate, or chloride) does not appear to affect its activity.[2,5,6]

The oral administration of gallium salts is disclosed in the art as requiring high dosages of the gallium salt to effect the requisite blood levels of gallium.[1,3] Bernstein[10], however, discloses that neutral gallium 3-hydroxy-4-pyrone complexes provide enhanced bioavailability of gallium when orally administered.

Notwithstanding the above, a clinical basis of certain mammalian diseases is the excessive proliferation of keratinocytes. In normal skin, continued regeneration of the epidermal layer is controlled by the limited production of keratinocytes wherein a portion of these keratinocytes then differentiate and move to the top of the skin, where they become cornified and die. These dead cells are eventually shed from the skin and the entire process occurs over approximately a 28 to 30 day period.

However, psoriasis is characterized by excessive proliferation of epidermal keratinocytes with a corresponding reduction in cell differentiation. The cells typically move to the top of the skin in only about three to six days. These excessive skin cells pile up, forming elevated, red scaly lesions characteristic of psoriasis, commonly covered by white scaly patches of dead skin cells. The overall effect of this condition is unsightly to disfiguring, scaly, sometimes itchy areas on the body predominantly located on the torso, elbows, etc., but that can appear on any area of skin and that can, in severe cases, cover large parts of the body.

The present invention is based on the discovery that neutral gallium chelates, at sufficiently high concentrations, inhibit proliferation of keratinocytes and therefore are useful in treating or preventing disease conditions associated with hyperproliferation of skin cells, particularly those disease conditions associated with hyperproliferation of keratinocytes. Such disease conditions associated with hyperproliferation of keratinocytes of particular interest herein are psoriasis, atopic dermatitis, contact dermatitis, eczematous dermatitis, seborrhoeic dermatitis, and Lichen planus. The topical pharmaceutical compositions of the invention are also useful in preventing or treating other skin conditions associated with hyperproliferation of keratinocytes, including as examples: hyperkeratosis, erythrokeratoderma, ichthyosis, actinic keratosis, acne, basal cell carcinoma, and squamous cell carcinoma. Diseases associated with hyperproliferation of cells from other cell lines, such as, for example, mast cells, melanocytes, fibroblasts, Langerhans cells, endothelial cells, epithelial cells, nerve cells, and Merkel cells, can also be treated via the present invention.

Regarding the psoriatic condition, evidence suggests that, in some cases, psoriasis is an autoimmune disease and, accordingly, some investigators have suggested that therapies such as the administration of immunomodulators toward T-lymphocytes and macrophages might be useful. In this regard, gallium salts such as gallium nitrate have been disclosed as useful in inhibiting experimental autoimmune encephalomyelitis[7] and in the prevention of rheumatoid arthritis[8]. However, there is no recognized correlation between immunomodulating activity and inhibition of keratinocyte proliferation. Furthermore, data presented herein demonstrate inhibition of keratinocyte proliferation by neutral gallium chelates in the absence of T-lymphocytes, macrophages, and other such cells of the immune system.

SUMMARY OF THE INVENTION

This invention is directed to the discovery that certain neutral gallium chelates, when used at a sufficient concentration, inhibit the proliferation of keratinocytes. Accordingly, such chelates can be used to treat disease conditions characterized by excessive proliferation of keratinocytes such as psoriasis.

Surprisingly, while not being limited to any theory, the data below suggest that the active moiety is the chelated gallium complex rather than elemental gallium and/or unbound chelator. The data below further suggest that while neutral gallium chelates are capable of inhibiting keratinocyte proliferation, other gallium compounds, such as gallium nitrate, are not.

In view of the above, in one of its method aspects, this invention is directed to a method for inhibiting proliferation of keratinocytes in mammalian skin which method comprises:

(a) identifying sites of excessive proliferation of keratinocytes in mammalian skin; and (b) applying to the skin sites identified in (a) above a topical pharmaceutical composition comprising a pharmaceutically acceptable excipient suitable for topical application and an effective amount of a 3-hydroxy-4-pyrone of formula 1:

to inhibit proliferation of keratinocytes, and wherein each R is independently selected from the group consisting of hydrogen and alkyl of from 1 to 6 carbon atoms.

Additionally, the neutral gallium chelates of this invention can be used prophylactically. In such methods, skin susceptible to conditions associated with hyperproliferation of keratinocytes is treated prior to any visible lesions on areas known to be susceptible to such lesions in a particular individual. When so employed, the methods of this invention comprise:

(a) identifying skin sites free of visible lesions but prone to lesions associated with hyperproliferation of keratinocytes; and (b) applying to the skin sites identified in (a) above a topical pharmaceutical composition comprising a pharmaceutically acceptable excipient suitable for topical application and an effective amount of a 3-hydroxy-4-pyrone of formula 1 as identified above.

In one of its composition aspects, this invention is directed to a topical pharmaceutical composition comprising a pharmaceutically acceptable excipient suitable for topical application and an effective amount of a 3-hydroxy-4-pyrone of formula 1:

to inhibit proliferation of keratinocytes, and wherein each R is independently selected from the group consisting of hydrogen and alkyl of from 1 to 6 carbon atoms.

Preferably, in the compound of formula I above, each R is independently hydrogen or alkyl of from 1 to 2 carbon atoms and, even more preferably, each R is independently hydrogen or methyl.

Surprisingly, the data below demonstrate that, at high concentrations, neutral gallium complexes of formula I above also promote keratinocyte differentiation and apoptosis. Such properties further teach the use of such neutral gallium complexes in the treatment of psoriasis and other disorders associated with excessive proliferation of skin cells, particularly those disorders associated with excessive proliferation of keratinocytes.

DETAILED DESCRIPTION OF THE INVENTION

As noted earlier, this invention is directed, in part, to methods to inhibit mammalian keratinocyte proliferation and, in particular, human keratinocyte proliferation by the topical administration of neutral gallium complexes of formula I above. However, prior to discussing this invention in further detail, the following terms will first be defined:

Definitions

As used herein, the following terms have the following definitions:

The term "keratinocyte" refers to skin cells having the capability to produce keratin, including, for example, cells known as basal cells, prickle cells, spinous cells, and granular cells, as well as all less-differentiated and more-differentiated variants of the same cell line, both normal and abnormal.

The term "neutral 3:1 gallium complex of a 3-hydroxy-4-pyrone" refers to an electrostatically neutral complex of $Ga^{+3}$ and 3 equivalents of the anionic form of 3-hydroxy-4-pyrone which complex is represented by the formula $[Ga^{+3}(py^{-1})_3]$ wherein $py^{-1}$ represents the anionic form of 3-hydroxy-4-pyrone which is defined below. Because such complexes do not dissociate to any significant extent in aqueous compositions maintained at a pH of from about 5 to about 9, these complexes remain predominantly electrostatically neutral in such compositions.

In this regard, these complexes are deemed "electrostatically neutral" because there are equal numbers of positive and negative charges in the complex, which does not readily dissociate into its anionic and cationic components.

Also, it is apparent that the anionic form of the 3-hydroxy-4-pyrone acts as a chelating agent to the gallium and as such, the complex is sometimes referred to herein as "neutral gallium chelates of 3-hydroxy-4-pyrones". It being understood that this latter term is synonymous with the term "neutral 3:1 gallium complex of a 3-hydroxy-4-pyrone".

The term "a 3-hydroxy-4-pyrone" refers to a compound of the Formula 2:

Formula 2 wherein from none to three of the hydrogen atoms attached to the ring carbon atoms are replaced by a hydrocarbon group of from one through six carbon atoms.

The term "pharmaceutically acceptable excipient" includes one or more excipients acceptable for use in the pharmaceutical composition.

Specific compounds encompassed by the term "a 3-hydroxy-4-pyrone" are represented by the Formulas 3–6 below:

Formula 3

Formula 4

Formula 5

Formula 6 wherein each R is independently a hydrocarbon of from 1 to 6 carbon atoms.

The unsubstituted form of 3-hydroxy-4-pyrone (Formula 3, also called pyromeconic acid) contains three hydrogen atoms that are bound only to ring carbon atoms. As noted above, any combination of these three hydrogen atoms can be substituted with a hydrocarbon group and all possible combinations of such substitutions are encompassed within this invention. The locations of a few possible substitutions are presented in Formulas 4–6, in which R is a hydrocarbon group (including methyl, ethyl, isopropyl, and n-propyl). The hydrocarbon groups are preferably acyclic and are preferably unbranched. Groups containing six or fewer carbon atoms, particularly of one through three carbon atoms, especially methyl or ethyl, are preferred. Single substitution is preferred; a substitution at either the 6-position or especially the 2-position is preferred. Some examples of specific compounds whose gallium complexes may be used in compositions comprised by the invention are: 3-hydroxy-2-methyl-4-pyrone (Formula 4, R=—CH$_3$—sometimes referred to as maltol or larixinic acid) and 3-hydroxy-2-ethyl-4-pyrone (Formula 4, R=—C$_2$H$_5$—sometimes referred to as ethyl maltol or ethylpyromeconic acid), both of which are preferred for use in this invention, especially 3-hydroxy-2-methyl-4-pyrone. Other preferred compounds include 3-hydroxy-4-pyrone (Formula 3—sometimes referred to as pyromeconic acid); and 3-hydroxy-6-methyl-4-pyrone (Formula 5, R=—CH$_3$).

The term "an anion of a 3-hydroxy-4-pyrone" refers to a compound defined in Formulas 3–6 above wherein the hydroxyl proton has been removed so as to provide for the anionically charged form of these compounds.

The term "gallium maltol" refers to the neutral 3:1 gallium complex of maltol.

The term "inhibit proliferation of keratinocytes" means that, as compared to control, the proliferation of keratinocytes is reduced by at least 20% in the in vitro assay of Example 2 below when assayed by crystal violet staining protocol. Preferably, the proliferation of keratinocytes is reduced by at least 35% and more preferably by at least 50% as compared to control.

Synthesis and Methodology

Methods for the preparation of neutral 3:1 gallium complexes of 3-hydroxy-4-pyrone or 3-hydroxy-4-pyrones wherein from one through three of the hydrogen atoms attached to ring carbon atoms are replaced by a hydrocarbon group containing from one through six carbon atoms are set forth in Bernstein[10]. Such methods comprise reacting such hydroxypyrones with gallium ions and isolating, at least in part, the resulting complex or complexes.

Specifically, the neutral 3:1 gallium complex of a 3-hydroxy-4-pyrone is prepared by the reaction of gallium ions and the 3-hydroxy-4-pyrones in solution. Gallium ions can be derived from a gallium salt, such as a gallium halide, particularly gallium chloride, or a gallium nitrate compound, especially a hydrated gallium nitrate. The gallium nitrate compounds are often preferable as they are easier to work with than gallium halides, which may be highly irritating and may react violently with many solvents, including water. Using the proper safeguards, a variety of gallium salts can be used. The reaction is conveniently effected in a mutual solvent, including but not limited to mixtures containing water, ethanol, methanol, and chloroform. Pure water may be used in many cases, though the purification of the gallium hydroxypyrone complexes may be difficult if it is used. A preferable method, if it is desired to separate at least a major part of reaction by-products such as sodium nitrates, sodium chloride, and sodium carbonates, is to use a mixture containing roughly equal parts of ethanol and chloroform, with a trace of water. The reaction by-products mentioned above have very low solubilities in this mixture and can be removed readily by filtration.

To produce the preferred neutral 3:1 hydroxypyrone:gallium complex, the hydroxypyrone and the gallium ions are mixed in 3:1 molar proportions, preferably with a slight excess of hydroxypyrone to insure a great preponderance of the 3:1 complex over the 2:1 and 1:1 complexes. The proportions of the particular complexes formed are dependent upon the pH of the solution. When a gallium salt such as a halide or nitrate is dissolved, the resulting solution will generally have a low pH. To form a preponderance of the preferred neutral 3:1 complex, a pH of from 5 to 9, preferably 6 through 7, is used. If a more acidic solution is used, the neutral 3:1 complex may not be as stable, even if a large excess of hydroxypyrone is present. Under highly basic conditions, poorly soluble gallium hydroxides may precipitate. It is preferable to regulate the pH with materials other than hydroxides such as sodium hydroxide, as the use of such hydroxides may cause the precipitation of poorly soluble gallium hydroxides, which are not wanted, and the pH may actually be buffered at a low level by this precipitation. The use of a carbonate, especially sodium carbonate, is preferred to regulate the pH. The use of sodium carbonate in a solvent mixture containing ethanol and chloroform, for example, can result in the precipitation of sodium nitrates that are very slightly soluble in this mixture, and which can be filtered off if desired to help purify the solution containing the desired pharmaceutical compositions.

The reaction to form the hydroxypyrone-gallium complex in solution is generally complete within about five minutes at about 20° C. Gentle stirring or other agitation of the solution promotes a uniform, rapid reaction. Longer reaction times may be used if found necessary. Following the separation, if desired, of reaction by-products such as sodium nitrates, sodium chloride, and sodium carbonates (depending on the solvents and reactants used), the reaction mixture may be evaporated slowly in air or, more rapidly, through the use of a rotary evaporator or by freeze drying, as examples. After drying, the gallium complex or complexes will remain in solid form. Recrystallization can be accomplished, if desired, using a suitable solvent, including but not limited to chloroform, alcohols such as ethanol and methanol, ether, water, acetone, and mixtures containing such solvents. Suitable solvents will depend upon which particular gallium complex(es) and impurities are present, upon the impurities to be separated, and upon the temperature and other physical conditions.

It is noted that the mentioned methods are not the only ones that can produce hydroxypyrones and gallium complexes with hydroxypyrones and that various alternative methods may be used as will be apparent to those skilled in the art. Additionally, in preparing the neutral 3:1 complexes of gallium with 3-hydroxy-4-pyrone, a single 3-hydroxy-4-pyrone or a mixture of 3-hydroxy-4-pyrones can be used. However, preferably, only a single 3-hydroxy-4-pyrone is employed.

With regard to the preparation of 3-hydroxy-4-pyrones which are used as starting materials in the preparation of the neutral 3:1 complexes of gallium with 3-hydroxy-4-pyrones, certain of these compounds occur naturally and may be obtained by extraction from the natural sources. For example, maltol is found in the bark of the young larch tree (Larix decidua Mill.), and in pine needles, chicory, wood tars and oils, and roasted malt[12]. Certain of the 3-hydroxy-4-pyrones are available commercially, including maltol and ethyl maltol. Others can be made from pyromeconic acid as a starting material, which can be derived from the decarboxylation of meconic acid. Methods for preparing such other 3-hydroxy-4-pyrones are well known in the art. Additionally, it is noted that maltol and ethyl maltol are in widespread use as flavoring and fragrance-enhancing agents for foods, and have very low toxicities when taken orally.

Formulations

The neutral gallium complexes of 3-hydroxy-4-pyrone are formulated into topical pharmaceutical compositions by conventional methods well known in the art. Such topical compositions comprise compositions which are intended only for application onto the skin as opposed to other delivery means such as parenteral pharmaceutical compositions, orally deliverable pharmaceutical compositions and the like. Preferred topical pharmaceutical compositions include, by way of example, one or more pharmaceutically acceptable excipients suitable for topical application and an effective amount of the 3-hydroxy-4-pyrone of formula I above. Suitable compositions include, by way of example, powders, gels, lotions, creams, ointments, hydrophilic preparations, shampoos, etc.

Powders are antipruritic and have a cooling effect. Talc, which is found in many powders, is the most lubricating but is nonabsorbent. Cornstarch is less lubricating but is absorbent.

Lotions are suspensions of a powder in water that provide a protective drying and cooling effect. As the water evaporates, drying and cooling occur, and a film of powder is left. Lotions are especially useful in hairy and skinfold areas. Emollients are lotions that contain fats and oils that lubricate and soothe irritated skin.

Creams are emulsions of oil in water. Creams are water washable and completely absorbed into the skin. As the amount of water is reduced and the amount of water is increased, the substances become more viscous and are classified as ointments (i.e., oil-in-water emulsions). The three types of ointments are water-soluble, emulsifiable, and water-repellant. Ointments may be used as bases or lubricants. Ointments are more effective lubricants than oil in water creams. However, ointments are occlusive and are not recommended for oozing or infected areas. Lotions and creams are appropriate for weeping lesions, ointments are appropriate for dry lesions.

Hydrophilic preparations are preparations that absorb water and include, by way of example, commercially available preparations such as Eucerin™ (Beiersdorf, Inc., Norwalk, Conn., U.S.A.), Aquaphor™ (Beiersdorf, Inc., Norwalk, Conn., U.S.A.), Lubriderm™ (Warner Lambert Company, Morris Plains, N.J.) and anhydrous lanolin.

Shampoos are aqueous compositions comprising one or more fatty acid salts (soap) and other optional additives such as perfumes, medicaments, etc.

In any event, the amount of the neutral gallium complex incorporated into the pharmaceutical composition is an amount sufficient to inhibit proliferation of keratinocytes. Preferably, as shown below, a solution concentration of at least $5 \times 10^{-5}$M for the neutral gallium complex in the skin is sufficient to provide inhibition of keratinocyte proliferation. Preferably, the pharmaceutical composition provides a concentration of at least $5 \times 10^{-5}$M of the neutral gallium complex to the skin. One means to estimate the required concentration of the neutral gallium complex in the topical pharmaceutical formulation that is needed to achieve such a concentration within the skin is to first estimate the volume of skin to be treated. For example, the thickness of epidermis and papillary dermis is typically about 0.04 cm in humans (ranging from about 0.01 cm on the eyelid to about 0.1 cm on the sole of the foot). The volume of skin in the treatment area is easily calculated, by multiplying the estimated thickness by the surface area of skin to receive the topical pharmaceutical composition. Using this value for the volume of skin to be treated, the concentration of neutral gallium complex in the topical pharmaceutical composition required to deliver any desired concentration of neutral gallium complex is readily calculated. For example, to deliver a concentration of $10^{-1}$M of the neutral gallium complex gallium maltol (GaM) to a patch of skin having a surface area of 75 cm$^2$ and a thickness of 0.04 cm (and thus a volume of 3 cm$^3$), about 0.13 mg of GaM (molecular weight 445.03) is needed (approx. 445.03 mg/cm$^3$/mole $\times$ $10^{-4}$ mole$\times$3 cm$^3$). If 0.13 mg GaM is present in 1 g of topical pharmaceutical composition, then the concentration of GaM is about 0.013 weight percent (w/w). Preferably, the neutral gallium chelates will comprise from about 0.0001 to about 5 weight percent of the topical pharmaceutical composition based on the total weight of the composition and more preferably from about 0.005 to about 0.5 weight percent.

Utility

Topical pharmaceutical compositions of this invention are useful to treat disease conditions mediated by excessive proliferation of skin cells, particularly those disease conditions associated with hyperproliferation of keratinocytes. Such disease conditions associated with hyperproliferation of keratinocytes of particular interest herein are psoriasis, atopic dermatitis, contact dermatitis, eczematous dermatitis, seborrhoeic dermatitis, and *Lichen planus*.

The topical pharmaceutical compositions of the invention are also useful in preventing or treating other skin conditions associated with hyperproliferation of keratinocytes, including as examples: hyperkeratosis, erythrokeratoderma, ichthyosis, actinic keratosis, acne, basal cell carcinoma, and squamous cell carcinoma. Diseases associated with hyperproliferation of cells from other cell lines, such as, for example, mast cells, melanocytes, fibroblasts, Langerhans cells, endothelial cells, epithelial cells, nerve cells, and Merkel cells, can also be treated via the present invention.

When so employed, an effective amount of the pharmaceutical composition is applied to the affect area at least once a day and preferably 1 to 3 times daily. The specific dose employed is regulated by the particular condition being treated as well as by the judgment of the attending clinician depending upon factors such as the severity of the condition, the age and general condition of the patient, and the like. In a preferred embodiment, the treatment of psoriasis employs a concentration of the neutral gallium chelate of 3-hydroxy-4-pyrone in the pharmaceutical composition sufficient to provide a solution concentration of at least about $5 \times 10^{-5}$M.

As noted in the examples below, relatively high concentrations of the neutral gallium chelates in the compositions of this invention also impart apoptosis to cells with this composition and, in the case of keratinocytes, facilitate cell differentiation. Both properties further illustrate beneficial use of such compositions in the treatment of psoriasis and other disorders associated with excessive proliferation of skin cells, particularly those disorders associated with excessive proliferation of keratinocytes.

EXAMPLES

The following examples are set forth to illustrate the claimed invention and are not to be construed as a limitation thereof.

Unless otherwise stated, all temperatures are in degrees Celsius. Also, in these examples, unless otherwise defined below, the abbreviations employed have their generally accepted meaning:

| | |
|---|---|
| Å | = angstroms |
| ATA | = aurin tricarboxylic acid |
| CAM | = camptothecin |
| cm | = centimeters |
| DDT | = dithiotreitol |
| HKGS | = human keratinocyte growth supplement (available from Cascade Biologics, Portland, Oregon, USA) |
| M | = molar |
| mg | = milligram |
| mL | = milliliter |
| mM | = millimolar |
| nm | = nanometers |
| PBS | = phosphate buffered saline |
| SDS | = sodium dodecyl sulfate |
| µL | = microliters |
| µm | = micron |
| v/v | = volume to volume |
| w/v | = weight to volume |
| w/w | = weight to weight |

In the examples below, culture medium 154 refers to a culture medium used as one component of a complete culture environment for the growth of normal human epidermal keratinocytes which is commercially available from, for example, Cascade Biologics, Portland, Oreg., U.S.A. as catalog number M-154-100.

Example 1

Preparation of Gallium Maltol

Maltol is dissolved in chloroform to form a 0.75M solution, and gallium nitrate nonohydrate is dissolved in ethanol to form a 0.5M solution. To 20 mL of the 0.75M maltol solution is slowly added, with continuous stirring, 10 mL of the 0.5M gallium nitrate nonohydrate solution. The resulting solution is stirred for 5 minutes at 23° C. Approximately 5.5 g (a large excess) of powdered Na$_2$CO$_3$ is added with stirring to raise the pH to close to 7. When the sodium carbonate is added, a trace of water may sometimes need to be added to facilitate the reaction, which is evidenced by some effervescence. Stirring is then continued for an additional ten minutes. The mixture is filtered to remove all solids, and the filtrate is evaporated in a rotary evaporator. The remaining crystalline solid is the 3:1 maltol:gallium composition. This composition is analyzed using powder x-ray diffraction and found to consist of orthothrombic crystals with unit cell dimensions of about a=18.53(1)Å, b=16.96(1)Å, c=12.05(1)Å. Crystallization from other solvents or under other conditions may produce other crystal structures. It is contemplated that amorphous structures can also be used in the methods and compositions of this invention.

Under some conditions, water may also be incorporated into the structure. The solubility of this composition is measured as about 24 millimolar in distilled deionized water at 23° C. The complex can be recrystallized from ethanol or other solvents to increase purity.

The gallium maltol complex of this example is a completely chelated structure sometimes referred to as a neutral chelate since the charge on the gallium is shielded by the three maltol groups.

Example 2

Inhibition of Growth of Cultured Keratinocytes by Gallium Maltol

Adult human keratinocytes from pooled donor skin were obtained from commercial sources (Cascade Biologics, Portland, Oreg., U.S.A.) and placed in 150 cm$^2$ bottom area culture flasks using culture medium 154 supplemented with HKGS (about 1%). At 80% confluency, cells were harvested with trypsin and cryopreserved until required.

At the start of the experiments, the required number of vials of keratinocytes was thawed, and the keratinocytes were placed in culture in 24 well plates at about 2,500 cells/cm$^2$ using the same culture medium as described above. After 24 hours (to allow attachment), the medium was changed to fresh 154 supplemented with HKGS (about 1%) and gallium maltol. Specifically, the fresh medium was prepared by addition of a sufficient amount of a stock solution to provide for six different compositions having a final gallium concentration of $10^{-4}$M, $10^{-5}$M, $10^{-6}$M, $10^{-8}$M, $10^{-10}$M, and $10^{-12}$M. The stock solution was prepared by adding 22.25 mg of gallium maltol to 50 mL of 154 medium and then passing the solution through a 0.2 μm filter and storing at 4° C.

Media were replaced every 2 or 3 days. Control cells did not receive any gallium maltol.

When control cells were about 40% confluent (generally at 4–5 days in culture, all media were removed by aspiration, keratinocyte growth was assayed by crystal violet staining and conversion to cell numbers as described by Wilkinson, et al.[11]. Specifically, cell layers rinsed in PBS, which was also aspirated, and 4 drops of crystal violet solution added to each well. The crystal violet solution was prepared by dissolving crystal violet (Fisher Scientific) in PBS:formaldehyde:ethanol (67:3:30%) to give a 0.5 w/v solution. A blank 24-well plate was treated similarly.

Cell number was also assayed in a separate, confirmatory experiment by hexosaminidase activity as described by Landegren.[12] Specifically, cells were grown and treated with gallium maltol as described above and then hexosaminidase was employed in place of crystal violet and processing was continued as above.

Figure 1:
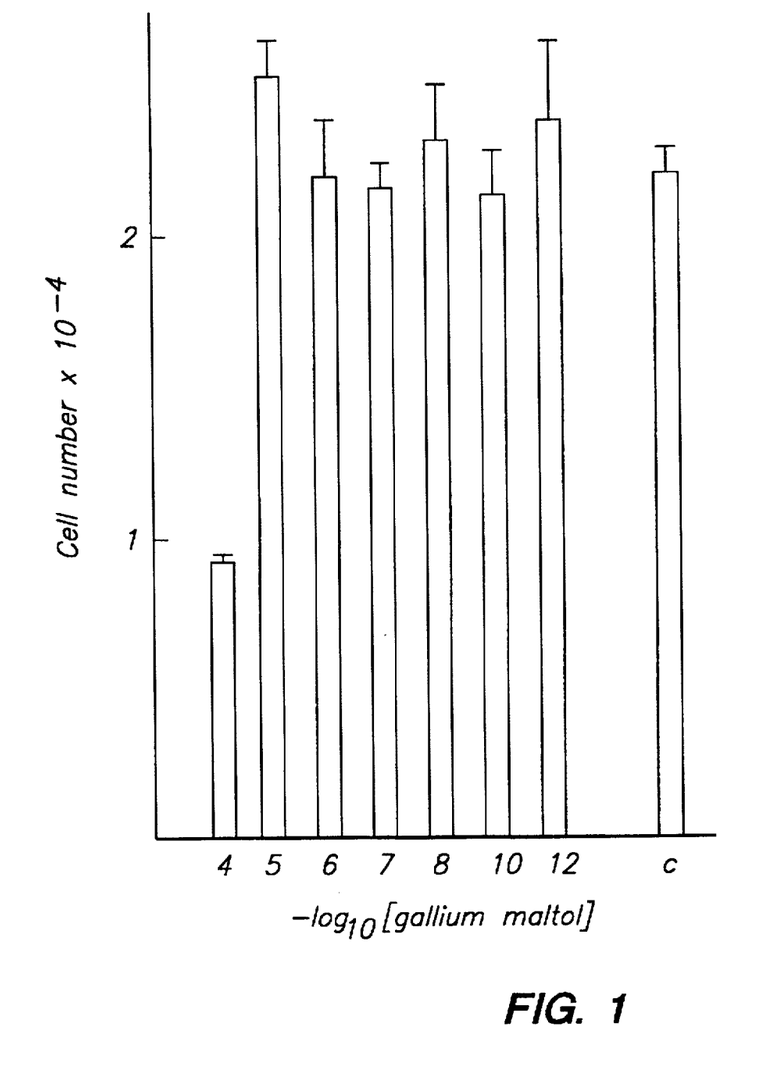
FIG. 1 illustrates the effects on keratinocyte growth in the presence of different concentrations of gallium maltol using the crystal violet method to determine cell growth.
Figure 2:
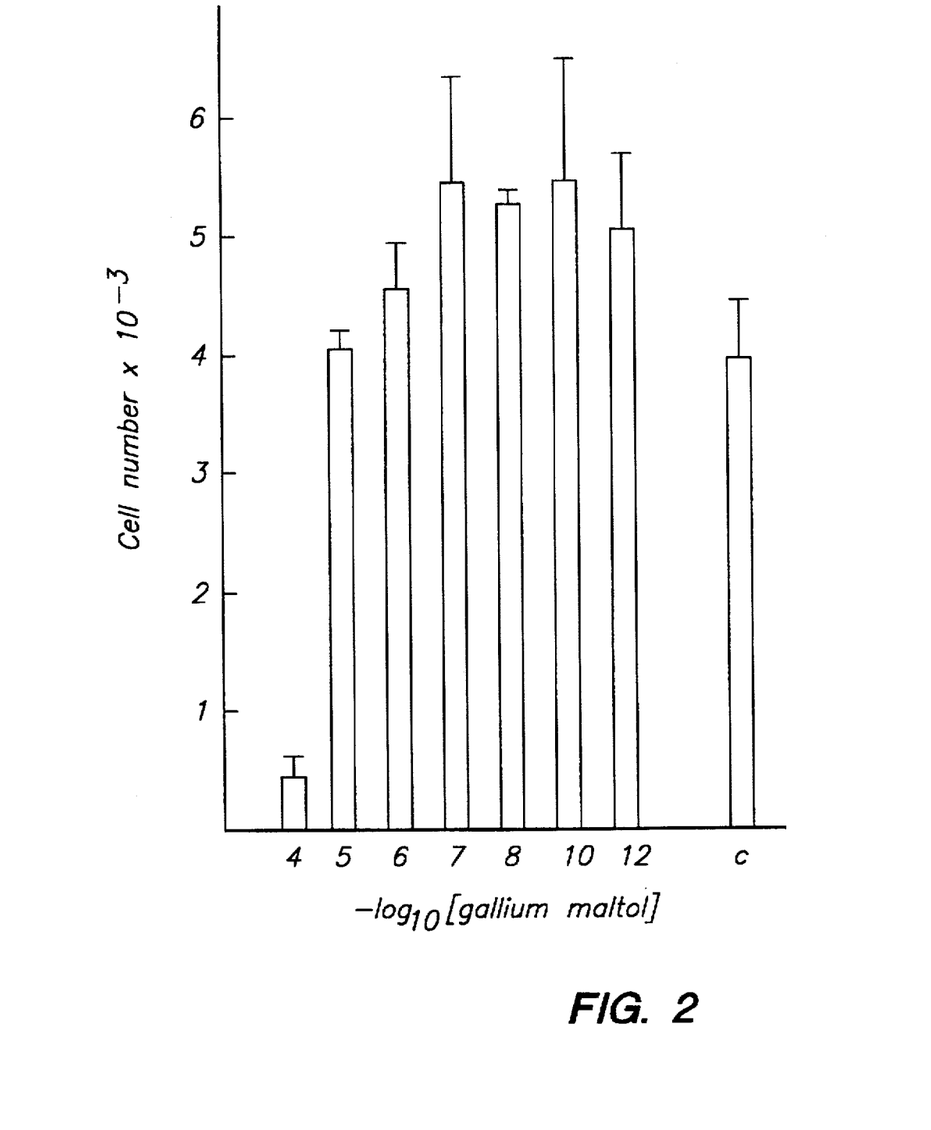
FIG. 2 illustrates the effects on keratinocyte growth in the presence of different concentrations of gallium maltol using the hexosaminidase method to determine cell growth.

Keratinocyte growth in the presence of gallium maltol is graphically illustrated in FIG. 1 (crystal violet) and FIG. 2 (hexoaminidase). The results set forth therein illustrate that gallium maltol only inhibits keratinocyte growth at high concentrations where, at $10^{-4}$M concentration of gallium maltol, keratinocyte growth was reduced by 60 to 90 percent as compared to control (c). At lower concentrations, the data in FIG. 2 suggests that gallium maltol may, in fact, slightly promote keratinocyte growth.

Example 3

Comparison of Keratinocytes Growth Inhibition by Gallium Maltol and Gallium Nitrate Keratinocytes were cultured in 24-well plates for 9 days in the manner described above in Example 2. After the first 24 hours in culture, medium 154 was changed to high $Ca^{+2}$ medium (1M $Ca^{+2}$) either without any additions (control "C") or supplemented with $1\times10^{-4}$M gallium maltol (GaM) or $1\times10^{-4}$M gallium nitrate (Ga) or with $3\times10^{-4}$M maltol (M).

Figure 3:
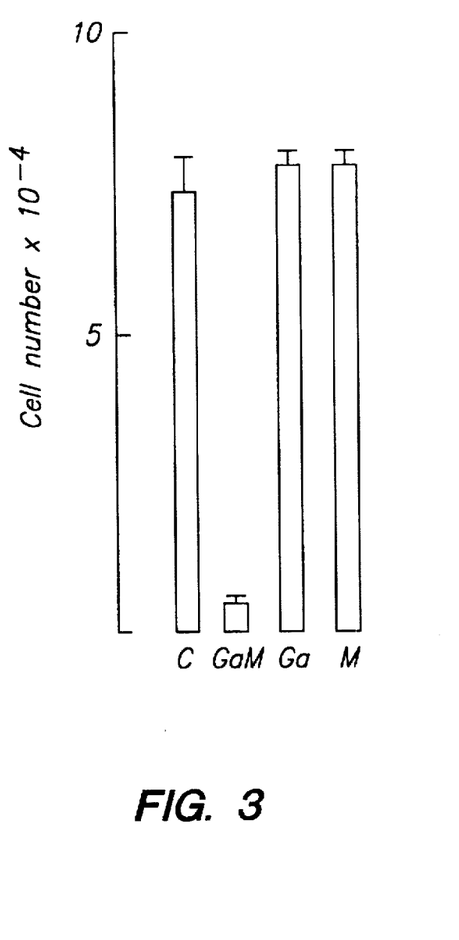
FIG. 3 illustrates the effect on keratinocyte proliferation by concentrations of $1 \times 10^{-4}$M gallium maltol (GaM) and gallium nitrate (Ga) and $3 \times 10^{-4}$M maltol (M).

The cells were then cultured and subsequently evaluated for inhibition of keratinocyte proliferation in the manner described above. The results of this evaluation are set forth in FIG. 3 which illustrates that neither gallium nitrate nor maltol had any effect on keratinocyte proliferation but gallium maltol inhibited such proliferation by about 94%. These data demonstrate that neither elemental gallium nor maltol per se are effective in reducing keratinocyte proliferation notwithstanding the use of the same concentration of both gallium and maltol as found in the neutral gallium maltol complex.

Example 4

Effect on Cell Differentiation by Gallium Maltol

Culture flasks (75 cm$^2$ bottom area) were seeded with keratinocytes at about 2,500 cells per cm$^2$ as before. After 24 hours, the medium in three (3) flasks were changed to media (154) with the calcium content increased from the normal 0.2 mM to 1.0 mM ("high calcium") plus gallium maltol (GaM) at the following concentrations: $1\times10^{-5}$M, $5\times10^{-5}$M, and $1\times10^{-4}$M. The culture was continued for 7 days when cells were about 75% confluent in the controls (no GaM). Media supplemented as above were changed every 2 days. Finally, media were aspirated and cells rinsed with PBS before exposure to trypsin (0.025%)/EDTA (0.01%). When dislodged, they were collected in centrifuge tubes and the flasks rinsed with PBS:trypsin neutralizing solution (Clonetics, San Diego, Calif., U.S.A.; 1:1 v/v) and added to the cell suspension. The total volume of suspensions was approximately 8 to 10 mL. Aliquots of these suspensions were counted on the hemocytometer in terms of:

(1) small, light or dark keratinocytes, referred to as "proliferating";

(2) larger, squamous keratinocytes, with intracellular structural elements; and (3) clear squamous cells without structural elements.

After counting, each suspension was centrifuged, the supernatant discarded, and the cell pellet resuspended in 0.5 to 1.0 mL of 1% SDS:2.5 mM DTT. After 15 minutes at 37° C., aliquots of these suspensions were counted for insoluble cornified envelops. The volumes were noted.

In a subsequent experiment, flasks of keratinocytes were grown in medium 154 for 4 days after seeding, before switching to the high calcium medium without gallium maltol (control) or with gallium maltol at final concentrations of $5\times10^{-5}$, $1\times10^{-5}$ or $1\times10^{-6}$M. There were 2 or 3 flasks in each group. Culture was continued for another 3 days, when the keratinocytes were harvested and counted as before.

Figure 4:
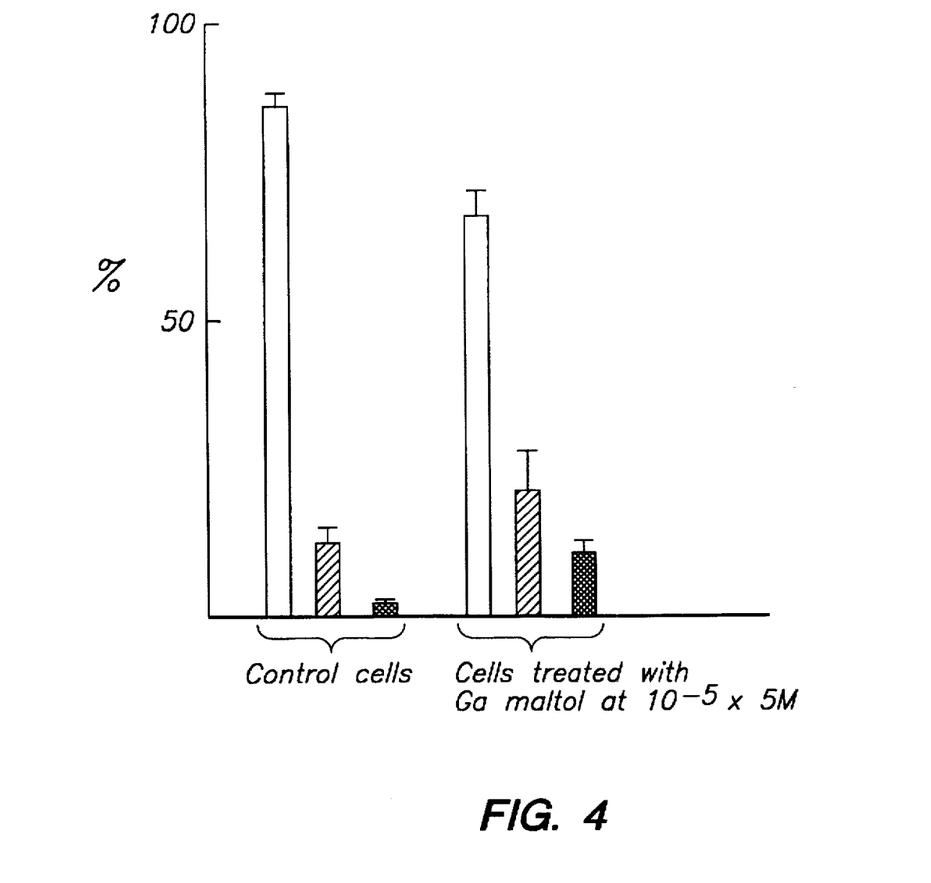
FIG. 4 illustrates the percentage occurrence of proliferative (white bars), squamous with intracellular structure (shaded bars), and clear squamous (black bars) keratinocytes in cultures grown in the presence of gallium maltol ($5 \times 10^{-5}$M). Values are means±standard deviation of 3 flasks in each case.

The results of this example are provide in FIG. 4 which illustrates the relative occurrence of proliferative, squamous and clear squamous cells. The data found in this figure demonstrates that there was a moderate decrease in the proportion of proliferative cells, increase in the number of squamous cells and about a tenfold increase in the number of cornified envelopes for the culture containing $5\times10^{-5}$M gallium maltol as compared to control. Also, the total number of cells in this culture decreased by about 90%.

These results demonstrate that concentrations of gallium maltol greater than $1\times10^{-5}$M advantageously enhance cell differentiation of keratinocytes. These results also demonstrate that at a gallium maltol concentration of greater than $1\times10^{-5}$M and preferably at a concentration of at least $5\times10^{-5}$M, inhibition of keratinocyte proliferation is achieved.

In contrast thereto, the number of proliferative, squamous and cornified cells in the culture containing $1\times10^{-5}$M gallium maltol was, for all intents and purposes, unchanged compared to control. Table I below illustrates these results at $1\times10^{-5}$M.

TABLE I

| CELL TYPE | CELL NUMBER | |
|---|---|---|
| | control | $10^{-5}$M gallium maltol |
| proliferative | 85.3 ± 2.7% | 83.6 ± 0.64% |
| squamous | 12.7 ± 2.7% | 13.5 ± 0.65% |
| clear squamous | 1.8 ± 0.9% | 2.9 ± 0.15% |
| cornified | 0.26 ± 0.01% | 0.39 ± 0.17% |

At a concentration of $1\times10^{-4}$M, the anti-proliferative effect of the gallium maltol was so great that the number of cells was too small for accurate counting.

In the experiment where keratinocytes were grown in culture for 4 days prior to addition of gallium maltol at concentrations of $5\times10^{-5}$M, $1\times10^{-5}$M, and $1\times10^{-6}$M and then continuing the culture for 3 additional days, no significant differences were observed in cell differentiation as determined by the proportion of cells. These results are set forth in Table II below:

TABLE II

| CELL TYPE | CELL NUMBER | | |
|---|---|---|---|
| | control | $1\times10^{-5}$M gallium maltol | $5\times10^{-5}$M gallium maltol |
| proliferative | 83.6 ± 3.0% | 80.8 ± 2.0% | 82.4 ± 0.91% |
| squamous | 13.3 ± 2.6% | 16.0 ± 3.1% | 14.0 ± 1.1% |
| clear squamous | 2.0 ± 0.03% | 3.1 ± 0.06% | 3.5 ± 0.06% |
| cornified | N/D | N/D | N/D |

N/D = not determined

In view of these results, cells treated with gallium maltol at a concentration of $1\times10^{-6}$M were not counted.

Example 5

Induction of Apoptosis by Gallium Maltol

The induction of apoptosis is a critical feature in the programmed cell death as it relates to disease conditions such as cancer, psoriasis, etc. where the uncontrolled proliferation of "immortal" cells such as keratinocytes is a causative feature of the disease. This example compares the ability of gallium maltol to induce apoptosis as compared to negative control (no gallium maltol), and positive control (CAM—an agent known to strongly induce apoptosis). The ability for gallium maltol to effect apoptosis was also measured by the inhibitory effect of ATA.

Specifically, keratinocyte cells were grown using medium 154 in 24 well plates seed with 2,500 cells/cm$^2$ as described above. Cultures were continued for 3 or 6 days when the cells had achieved about 20 or 60% confluence respectively. On these 2 occasions, media were aspirated from groups of 3 or 4 wells and replaced with high $Ca^{+2}$ medium either without supplement or with one of the following supplements:

1. Gallium maltol at a final concentration of one of the following: (a) $5\times10^{-4}$M, (b) $1\times10^{-4}$M, (c) $5\times10^{-5}$M, (d) $1\times10^{-5}$M, and (e) $1\times10^{-6}$M;
2. CAM at $1\times10^{-5}$ or $1\times10^{-6}$M;
3. ATA at $1\times10^{-4}$M;
4. As in (3) plus CAM at $1\times10^{-5}$ or $1\times10^{-6}$M; and
5. As in (3) plus gallium maltol at $1\times10^{-4}$ or $2.5\times10^{-4}$M;

Culture was renewed for a further 24 hours. At this time, media were removed and discarded, and the cells lysed with 200 μL/well of the solution provided in the Cell Death Detection Kit ELISA Plus (Boehringer Mannheim Biochemicals, Indianapolis, Ind., U.S.A., catalogue number 1774425). Aliquots of the lysate (20 μL) from each of 2 or 3 wells were assayed for nucleosomal enrichment following the kit instructions.

Figure 5:
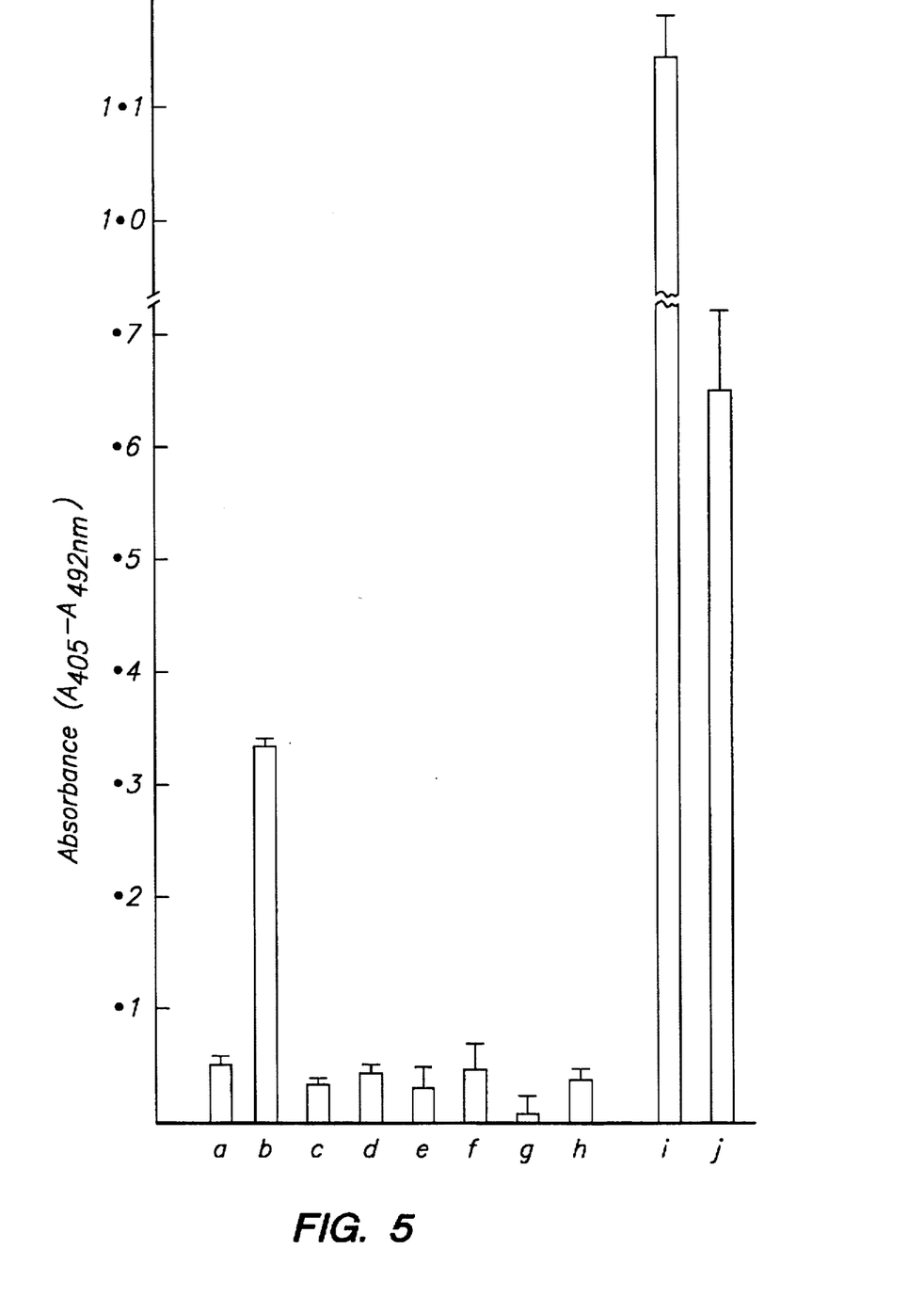
FIG. 5 illustrates the extent of apoptosis in keratinocytes cultured for 3 days prior to exposure to different concentrations of gallium maltol; different concentrations of CAM; a concentration of ATA of $1 \times 10^{-4}$M; a concentration of ATA of $1 \times 10^{-4}$M plus CAM at $1 \times 10^{-5}$ or $1 \times 10^{-6}$M; and a concentration of ATA of $1 \times 10^{-4}$M plus gallium maltol at $1 \times 10^{-4}$ or $2.5 \times 10^{-4}$M.

The extent of occurrence of apoptosis in keratinocytes cultured for 3 days prior to treatment under various conditions is indicated in FIG. 5. In this figure, the bars represent the absorbance at 405 nm (less absorbance at 492 nm) of the substrate reaction mixtures in the cell death assay of cells treated as above with media containing:

a) control, no additives
b) gallium maltol at a concentration of $5\times10^{-4}$M
c) gallium maltol at a concentration of $1\times10^{-4}$M
d) gallium maltol at a concentration of $5\times10^{-5}$M
e) gallium maltol at a concentration of $1\times10^{-5}$M
f) gallium maltol at a concentration of $1\times10^{-6}$M
g) $1\times10^{-4}$M ATA
h) $1\times10^{-4}$M ATA+gallium maltol at a concentration of $1\times10^{-4}$M
i) $1\times10^{-5}$M CAM
j) $1\times10^{-5}$M CAM+ATA at a concentration of $1\times10^{-4}$M In FIG. 5, values are means+standard deviation (N=2). The higher the absorbance differential between the absorbance at 405 nm minus the absorbance at 492 nm corresponds to a greater degree of apoptosis.

The results of FIG. 5 demonstrate that gallium maltol, when employed at a concentration of $5\times10^{-4}$M, gave about a 7 fold increase in apoptosis compared to control but that the use of lower concentrations of gallium maltol failed to provide such a significant increase in apoptosis. FIG. 5 further illustrates that $1\times10^{-5}$M CAM strongly induced apoptosis which was reduced by half by $1\times10^{-4}$M ATA.

Figure 6:
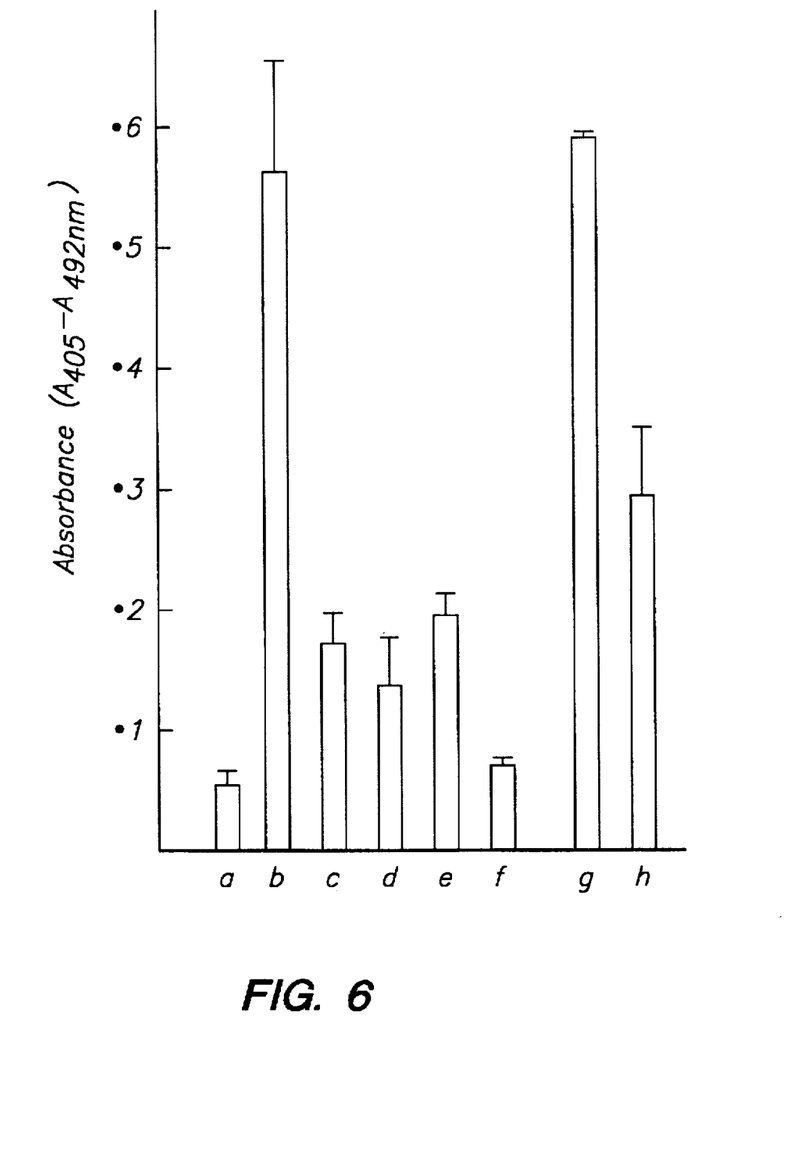
FIG. 6 illustrates the extent of apoptosis in keratinocytes as in FIG. 5 except that the cells were cultured for 6 days.

The extent of occurrence of apoptosis in keratinocytes cultured for 6 days prior to treatment under various conditions is indicated in FIG. 6. The longer culture time was employed to permit a greater number of cells to grow. In this figure, the bars represent the absorbance at 405 nm (less absorbance at 492 nm) of the substrate reaction mixtures in the cell death assay of cells treated as above with media containing:

a) control, no additives
b) gallium maltol at a concentration of $5\times10^{-4}$M
c) gallium maltol at a concentration of $2.5\times10^{-4}$M d) gallium maltol at a concentration of $1\times10^{-4}$M e) gallium maltol at a concentration of $5\times10^{-5}$M f) gallium maltol at a concentration of $2.5\times10^{-4}$M+$1\times10^{-4}$M ATA g) $1\times10^{-6}$MCAM h) $1\times10^{-6}$M CAM+$1\times10^{-4}$M ATA In FIG. 6, values are means+standard deviation (N=3). The higher the absorbance differential between the absorbance at 405 nm minus the absorbance at 492 nm corresponds to a greater degree of apoptosis.

The results of FIG. 6 demonstrate that gallium maltol, when employed at a concentration of $5\times10^{-4}$M, gave about a 10 fold increase in apoptosis compared to control with smaller increases in apoptosis at lower concentrations of gallium maltol. FIG. 6 further illustrates that $1\times10^{-6}$M CAM strongly induced apoptosis which was reduced by half by $1\times10^{-4}$M ATA.

Example 6

Comparison of Apoptosis of Keratinocytes by Gallium Maltol, Gallium Nitrate and Maltol The evaluation of apoptosis of keratinocytes was conducted to determine the relative affect on apoptosis achieved by gallium maltol, gallium nitrate and maltol. Specifically, keratinocyte cells were seeded in 12 well plates seed using culture medium 154. Cultures were continued for 4 days and the medium was changed to medium 154 with 1.2 mM $Ca^{+2}$ either without supplement or with one of the following supplements:

1. gallium maltol at a final concentration of $5\times10^{-4}$M;
2. gallium nitrate at a final concentration of $5\times10^{-4}$M;
3. maltol at a concentration of $15\times10^{-4}$M; and
4. CAM at a concentration of $1\times10^{-5}$M.

Figure 7:
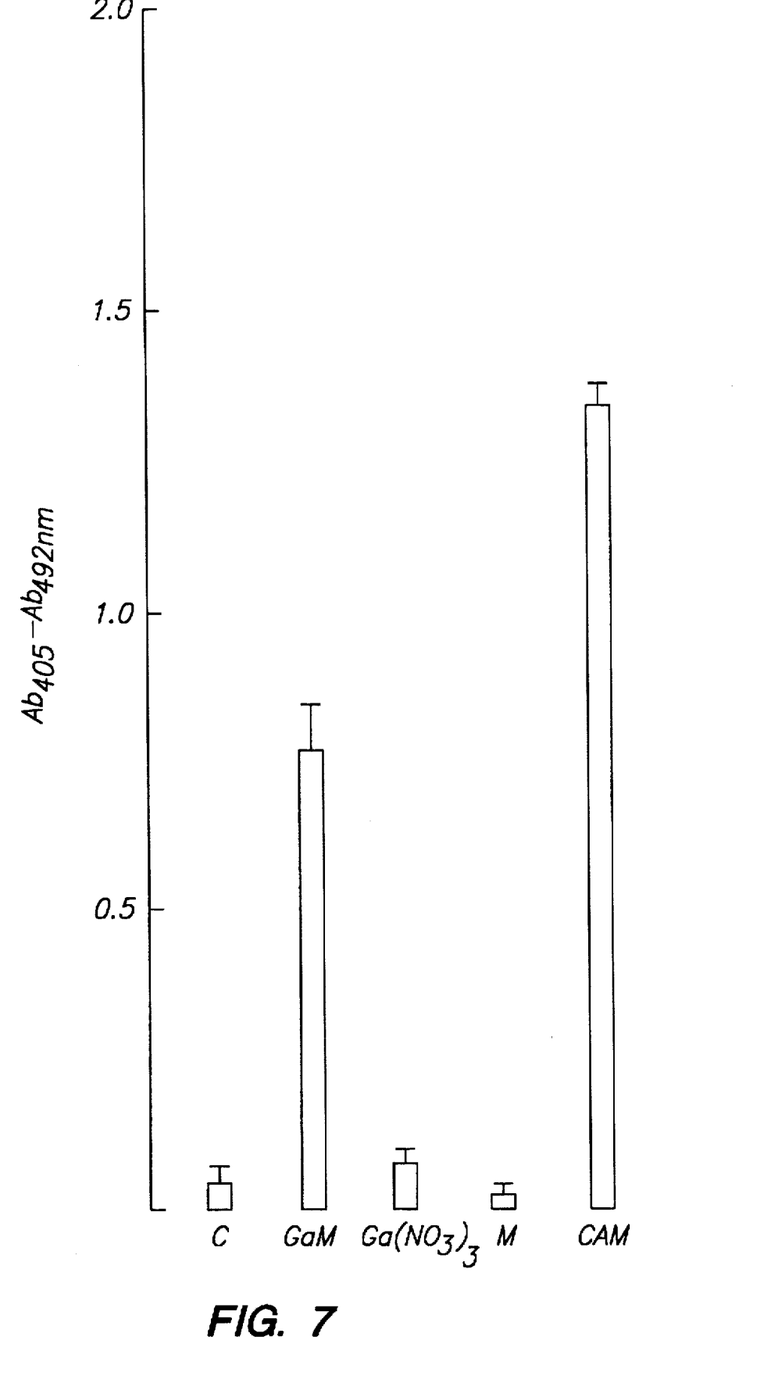
FIG. 7 compares the extent of apoptosis in keratinocytes in the presence of gallium maltol, gallium nitrate or maltol.

Three (3) wells were used in each group. The final amount of medium was 300 μL in each well. Culture was continued for 2 days. At this time, the amount of apoptosis was determined as above and the results are shown in FIG. 7. Bars represent absorbance at 405 nm minus the absorbance at 492 nm. The results of FIG. 7 demonstrate that gallium maltol, when employed at a concentration of $5\times10^{-4}$M, gave about a 19 fold increase in apoptosis compared to control but that the use of either gallium nitrate or maltol had no significant effect on apoptosis. These results are consistent with the conclusion that it is chelated neutral gallium maltol and not elemental gallium or the chelator maltol which beneficially impart apoptosis.

Example 7

Preparation of a Topical Pharmaceutical Composition Comprising Gallium Maltol

The following example illustrates one method which can be employed to prepare a hydrophilic pharmaceutical composition comprising gallium maltol which composition is suitable for topical application. In this example, commercially available Aquaphor™ (Beiersdorf, Inc., Norwalk, Conn., U.S.A.) is employed as the base formulation. To this formulation is added a sufficient amount of an aqueous solution of gallium maltol such that the final composition comprises 0.05 weight percent gallium and 7.5 weight percent added water based on the total weight of the composition. The composition is then mixed until homogeneous.

Although the foregoing invention has been described in some detail by way of illustration and example for purposes of clarity and understanding, it will be apparent that certain changes and modifications may be practiced within the scope of the appended claims.

What is claimed is:

1. A method for inhibiting proliferation of keratinocytes in mammalian skin which method comprises:

(a) identifying sites of excessive proliferation of keratinocytes in mammalian skin; and (b) applying to the skin sites identified in (a) above a topical pharmaceutical composition comprising a pharmaceutical excipient acceptable for topical application and an effective amount of a neutral gallium chelate of 3-hydroxy-4-pyrone represented by formula 1:

to inhibit proliferation of keratinocytes, and wherein each R is independently selected from the group consisting of hydrogen and alkyl of from 1 to 6 carbon atoms.

2. The method of claim 1 wherein each R is independently hydrogen or an unbranched alkyl group of from 1 to 3 carbon atoms.

3. The method of claim 2 wherein each R is independently hydrogen, methyl or ethyl.

4. The method of claim 2 wherein said 3-hydroxy-4-pyrone of formula 1 has a single alkyl substituent at either the 2 or 6 position thereof.

5. The method of claim 1 wherein said 3-hydroxy-4-pyrone of formula 1 is selected from the group consisting of 3-hydroxy-4-pyrone, 3-hydroxy-2-methyl-4-pyrone, 3-hydroxy-2-ethyl-4-pyrone, and 3-hydroxy-2-ethyl-4-pyrone.

6. The method of claim 5 wherein said 3-hydroxy-4-pyrone of formula 1 is 3-hydroxy-2-methyl-4-pyrone.

7. The method of claim 5 wherein said 3-hydroxy-4-pyrone of formula 1 is 3-hydroxy-2-ethyl-4-pyrone.

8. The method of claim 1 wherein said gallium chelate of 3-hydroxy-4-pyrone is present in the pharmaceutical composition at a concentration of at least $5\times10^{-5}$M.

9. The method of claim 1 wherein said gallium chelate of 3-hydroxy-4-pyrone is present in the pharmaceutical composition in an amount sufficient to achieve a concentration of at least $5\times10^{-5}$M of said gallium chelate in the skin.

10. The method according to claim 1 wherein said sites of excessive proliferation of keratinocytes in mammalian skin are associated with psoriasis.

11. The method according to claim 1 wherein said sites of excessive proliferation of keratinocytes in mammalian skin are associated with atopic dermatitis, contact dermatitis, eczematous dermatitis, seborrhoeic dermatitis, Lichen planus, hyperkeratosis, erythrokeratoderma, ichthyosis, actinic keratosis, acne, basal cell carcinoma, or squamous cell carcinoma.

12. A method for inhibiting proliferation of keratinocytes in mammalian skin which method comprises:

(a) identifying sites of excessive proliferation of keratinocytes in mammalian skin; and (b) applying to the skin sites identified in (a) above a topical pharmaceutical composition comprising a pharmaceutical excipient acceptable for topical application and an effective amount of gallium maltol.

13. The method of claim 12 wherein said gallium maltol is present in the pharmaceutical composition at a concentration of at least $5\times10^{-5}$M.

14. The method of claim 12 wherein said gallium maltol is present in the pharmaceutical composition in an amount sufficient to achieve a concentration of at least $5\times10^{-5}$M of said gallium maltol in the skin.

15. The method according to claim 12 wherein said sites of excessive proliferation of keratinocytes in mammalian skin are associated with psoriasis.

16. A method to inhibit the hyperproliferation of keratinocytes in mammalian skin prior to the development of visible lesions associated with said hyperproliferation on skin areas known to be susceptible to such lesions which method comprises:

(a) identifying skin sites free of visible lesions but prone to lesions associated with hyperproliferation of keratinocytes; and (b) applying to the skin sites identified in (a) above a topical pharmaceutical composition comprising a pharmaceutically acceptable excipient suitable for topical application and an effective amount of a 3-hydroxy-4-pyrone of formula 1 as identified above.

17. A method for inhibiting undesired proliferation of mammalian cells selected from the group consisting of keratinocytes, mast cells, melanocytes, fibroblasts, Langerhans cells, endothelial cells, epithelial cells, nerve cells, and Merkel cells which method comprises:

(a) identifying sites of excessive proliferation of said cells in a mammal; and (b) administering to the sites identified in (a) above a pharmaceutical composition comprising a pharmaceutical acceptable excipient and an effective amount of a neutral gallium chelate of 3-hydroxy-4-pyrone represented by formula 1:

to inhibit proliferation of said cells, and wherein each R is independently selected from the group consisting of hydrogen and alkyl of from 1 to 6 carbon atoms.

* * * * *